(12) United States Patent
Proksa

(10) Patent No.: US 9,177,682 B2
(45) Date of Patent: Nov. 3, 2015

(54) DYNAMIC FILTER FOR COMPUTED TOMOGRAPHY (CT)

(75) Inventor: Roland Proksa, Neu Wulmstorf (DE)

(73) Assignee: Koninklijke Philips N.V., Eindhoven (NL)

( * ) Notice: Subject to any disclaimer, the term of this patent is extended or adjusted under 35 U.S.C. 154(b) by 120 days.

(21) Appl. No.: 13/825,410

(22) PCT Filed: Sep. 28, 2011

(86) PCT No.: PCT/IB2011/054268
§ 371 (c)(1),
(2), (4) Date: Mar. 21, 2013

(87) PCT Pub. No.: WO2012/042484
PCT Pub. Date: Apr. 5, 2012

(65) Prior Publication Data
US 2013/0182820 A1    Jul. 18, 2013

Related U.S. Application Data

(60) Provisional application No. 61/388,021, filed on Sep. 30, 2010.

(51) Int. Cl.
*A61B 6/03* (2006.01)
*G21K 1/10* (2006.01)
*A61B 6/00* (2006.01)
*G21K 1/04* (2006.01)
*G01N 23/04* (2006.01)

(52) U.S. Cl.
CPC . *G21K 1/10* (2013.01); *A61B 6/032* (2013.01); *A61B 6/4021* (2013.01); *A61B 6/4035* (2013.01); *A61B 6/5258* (2013.01); *G01N 23/046* (2013.01); *G21K 1/04* (2013.01)

(58) Field of Classification Search
CPC ........ A61B 6/032; A61B 6/4035; A61B 6/06; G01N 23/046; G21K 1/04; G21K 1/10
USPC .............................. 378/16, 156, 157, 158, 159
See application file for complete search history.

(56) References Cited

U.S. PATENT DOCUMENTS

| | | | |
|---|---|---|---|
| 4,752,879 A * | 6/1988 | Brunnett | .......................... 378/19 |
| 5,278,887 A | 1/1994 | Chiu et al. | |
| 6,501,828 B1 * | 12/2002 | Popescu | ........................ 378/150 |
| 7,076,029 B2 | 7/2006 | Toth et al. | |
| 7,313,217 B2 | 12/2007 | Toth et al. | |
| 7,706,508 B2 | 4/2010 | Arenson et al. | |

(Continued)

FOREIGN PATENT DOCUMENTS

| | | |
|---|---|---|
| EP | 0913839 A2 | 5/1999 |
| EP | 1356770 A1 | 10/2003 |

(Continued)

*Primary Examiner* — Glen Kao

(57) ABSTRACT

An imaging system including a source (310) having a focal spot (406) that emits a radiation beam that traverses an examination region, a radiation sensitive detector array (316) having a plurality of pixels that detects radiation traversing the examination region and generates projection data indicative of the detected radiation, and a filter (314), disposed between the source and the examination region, that filters peripheral regions of the emitted radiation, wherein the filter includes two separate and moveable regions (402), each region having a substantially same thickness and constant homogeneity.

13 Claims, 5 Drawing Sheets

(56) References Cited

U.S. PATENT DOCUMENTS

| | | | |
|---|---|---|---|
| 2003/0198319 A1* | 10/2003 | Toth et al. | 378/159 |
| 2004/0076265 A1* | 4/2004 | Heuscher et al. | 378/210 |
| 2004/0234021 A1* | 11/2004 | Hoffman | 378/4 |
| 2008/0205599 A1* | 8/2008 | Hashimoto | 378/148 |
| 2009/0074278 A1* | 3/2009 | Beaulieu et al. | 382/131 |

FOREIGN PATENT DOCUMENTS

| | | |
|---|---|---|
| FR | 2676584 A1 | 11/1992 |
| WO | 2009063353 A2 | 5/2009 |

\* cited by examiner

DYNAMIC FILTER FOR COMPUTED TOMOGRAPHY (CT)

CROSS REFERENCE TO RELATED APPLICATIONS

This application is a national filing of PCT application Serial No. PCT/IB2011/054268, filed Sep. 28, 2011, published as WO 2012/042484 A1 on Apr. 5, 2012, which claims the benefit of U.S. provisional application Ser. No. 61/388,021 filed Sep. 30, 2010, which is incorporated herein by reference.

The following generally relates to imaging and more particular to a filter utilized to reduce the radiation at the edges of the radiation beam in computer tomography (CT) scanners.

A conventional CT scanner includes an x-ray tube that emits radiation. A source collimator is disposed between the x-ray tube and an examination region and collimates the emitted radiation to produce a fan or cone shaped x-ray beam. The collimated beam traverses the examination region and an object or subject therein (which attenuates the beam as a function of the radiodensity of the object or subject) and illuminates a detector array disposed across the examination region from the x-ray tube. The detector produces projection data indicative of the detected radiation, and the projection data has been reconstructed to generate volumetric image data indicative of the object or subject.

A so-called bowtie filter has been positioned between the source collimator and the examination region and attenuates the fan or cone shape x-ray beam to a greater degree at the outer regions or periphery rays of the beam, thereby reducing the flux at the outer regions of the fan or cone beam. The name filter reflects the typical shape of the filter. Such filtering is well-suited for photon counting detectors, which suffer from insufficient count rate capabilities. By way of example, in a typical CT scan, excessive count rates are only required for rays of the beam that do not cross the subject or that travels only short distances through the subject in peripheral regions. Such filtering is also well-suited to be employed with scanners with non-counting detectors, for example, to improve radiation efficiency, etc.

FIGS. 1(A), 1(B) and 1(C) illustrate an example of a conventional static bowtie filter 102 in connection with an x-ray source 104, a source collimator 106, and an examination region 108, and a portion of a subject 110 being scanned. Theoretically, the filter 102 corresponds to the profile or shape of the subject being scanned, and heavily filters the regions of the beam that traverse only air, lightly filters the region of the beam that traverses the subject, and smoothly transitions the degree of filtering for transitions therebetween so that a correct x-ray profile can be achieved. An air scan is performed to measure the attenuation profile of the filter and generate a calibration based thereon for detector pixel normalization during reconstruction.

Unfortunately, the profile of every subject is not the same as the shape may be larger for some subject, smaller for other subjects, and may also be different such as more or less cylindrical as shown in FIGS. 1(A) and 1(C). Furthermore, the profile of the same subject may be quite different depending on the angle at which the subject is viewed as shown in FIGS. 1(A) and 1(B). As a consequence, the static filter may be better-suited for some subjects but not be well-suited for other subjects as the filter cannot match each subject. In addition, a subject may be positioned off-center such that a portion of the beam traversing air is lightly filtered, and a portion of the beam traversing the subject is heavily filtered. As a result, photon flux at the edges of the subject may decrease the fidelity of the detector output to a level that may be prohibitively low for diagnostically valuable images.

FIGS. 2(A), 2(B) and 2(C) illustrate an example of a dynamic bowtie filter 202 formed from two sub-filters $202_1$ and $202_2$, each having a higher attenuation region that smoothly transitions to a lower attenuation tail. With the illustrated dynamic filter, the sub-filters $202_1$ and $202_2$ linearly translate towards or away from each other to dynamically change the profile of the filter as shown in FIGS. 2(A) and 2(B). Note in FIG. 2(B) only the sub-filter $202_1$ (and not sub-filter $202_2$) is shown for clarity. In this example, the sub-filters $202_1$ and $202_2$ can be combined to create a profile similar to that of the static filter of FIG. 1 as show in FIG. 2(C).

Unfortunately, with the filter 202, a length of a ray from the focal spot to each position along a sub-filter changes with the location of the sub-filter and a thickness of the sub-filter for the ray also changes with the location of the sub-filter, rendering calibration of each pixel for the profile of the filter 202 a nightmare, and image quality is very sensitive to the precise knowledge of the bowtie influence in each single detector pixel.

Aspects of the present application address the above-referenced matters and others.

According to one aspect, an imaging system including a source having a focal spot that emits a radiation beam that traverses an examination region, a radiation sensitive detector array having a plurality of pixels that detects radiation traversing the examination region and generates projection data indicative of the detected radiation, and a filter, disposed between the source and the examination region, that filters peripheral regions of the emitted radiation, wherein the filter includes two separate and moveable regions, each region having a substantially same thickness and constant homogeneity.

According to another aspect, a method includes filtering peripheral rays, of an emitted radiation beam traversing an examination region, which substantially do not traverse an object or subject in the examination region, with a dynamically adjustable filter having a substantially same thickness and homogeneity along the filter.

According to another aspect, a method for reducing a flux of peripheral rays of a radiation beam includes identifying a location of the peripheral rays while scanning an object or subject, dynamically positioning a filter having a uniform thickness and substantially same homogeneity in a path of the peripheral rays, thereby filtering the peripheral rays with the dynamically positioned filter, and detecting radiation filtered by the filter and radiation not filtered by the filter and generating projection data indicative of the detected radiation.

The invention may take form in various components and arrangements of components, and in various steps and arrangements of steps. The drawings are only for purposes of illustrating the preferred embodiments and are not to be construed as limiting the invention.

Figure 3:
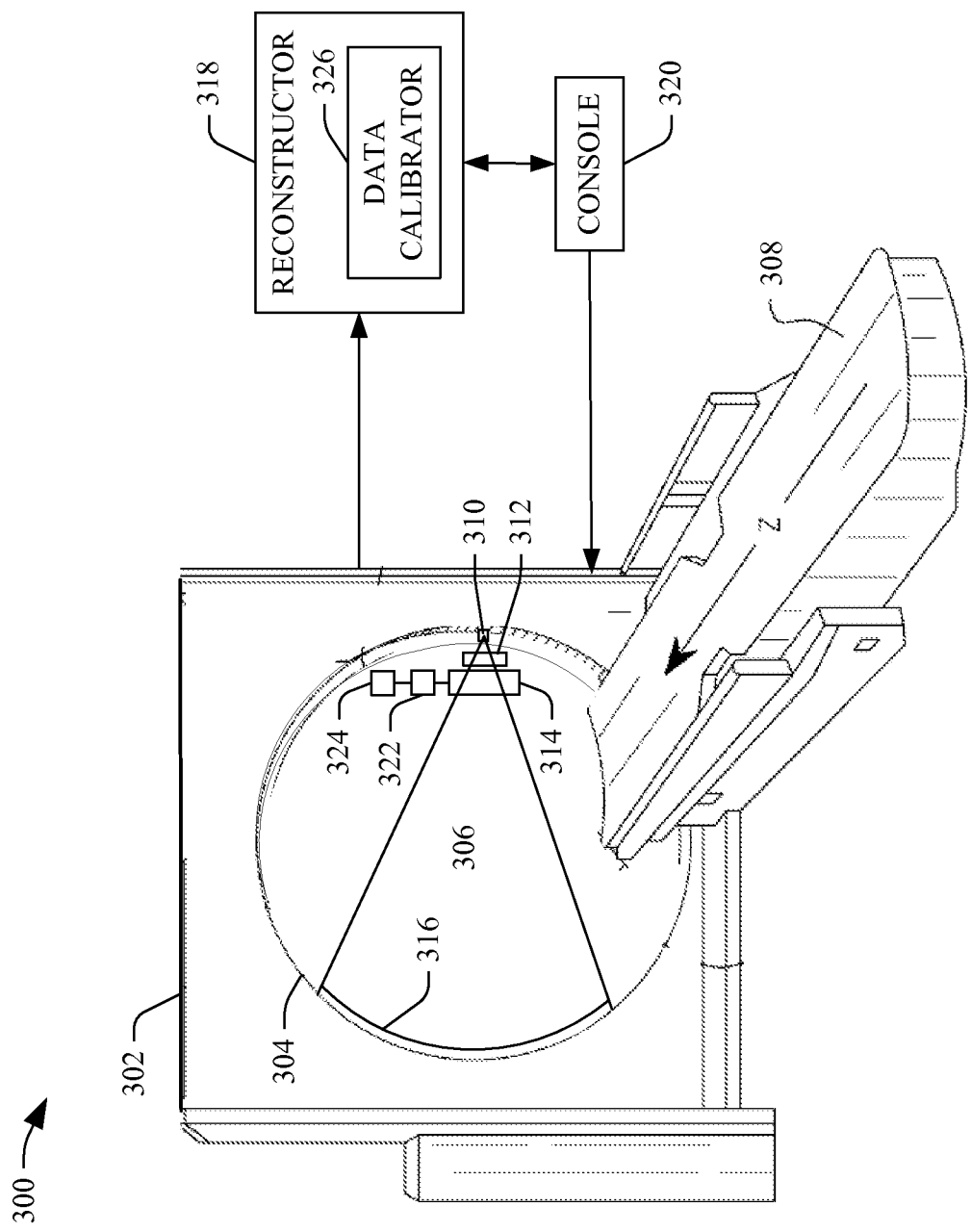
FIG. 3 illustrates an example imaging system including a dynamic filter having a uniform thickness and substantially constant homogeneity.

FIG. 3 illustrates an imaging system 300 such as a computed tomography (CT) scanner. The imaging system 300 includes a stationary gantry 302 and a rotating gantry 304, which is rotatably supported by the stationary gantry 302. The rotating gantry 304 rotates around an examination region 306 about a longitudinal or z-axis. A support 308, such as a couch, supports a subject in the examination region 306 and can be used to position the subject with respect to x, y, and/or z axes before, during and/or after scanning.

A radiation source 310, such as an x-ray tube, is supported by the rotating gantry 304 and rotates with the rotating gantry 304 about the examination region 306, and emits radiation that traverses the examination region 306. A source collimator 312 collimates the emitted radiation, forming a generally fan, cone, or other shaped beam that traverses the examination region 306. A radiation sensitive detector array 316 is located opposite the radiation source 310, across the examination region 306. The detector array 316 includes a plurality of detector pixels that detect radiation traversing the examination region 306 and generate or projection data indicative of the detected radiation.

A dynamic filter 314 is arranged between the collimator 312 and the examination region 306 and filters the collimated beam. As described in greater detail below, the dynamic filter 314 is configured to dynamically adjust its profile, through movement of one or more filter regions thereof, based on the shape of the object or subject being scanned, while mitigating impact on the filter attenuation normalization calibration. The movement of the one or more regions can be achieved through one or more motors 322 in mechanical communication with the one or more filter regions, and a controller 324 that controls the one or motors 322 to move, individually or concurrently, the one or more filter regions along predefined path such as a track, a rail, or the like.

A reconstructor 318 reconstructs the processed projection data and generates volumetric image data indicative of the examination region 306. The reconstructor 318 includes a data calibrator 326 for calibrating the detector pixels based on the profile of the dynamic filter 314. As described in greater detail below, various calibration algorithms can be employed, depending on whether a pixel detects fully filtered radiation, unfiltered radiation, or partly filtered/partly unfiltered radiation. The resulting volumetric image data can be processed by an image processor or the like to generate one or more images. A general purpose computing system serves as an operator console 320, and includes an output device such as a display and an input device such as a keyboard, mouse, and/or the like. Software resident on the console 320 allows the operator to control the operation of the system 300, for example, allowing the operator to select a protocol that employs the dynamic filter, initiate scanning, etc.

Figure 4:
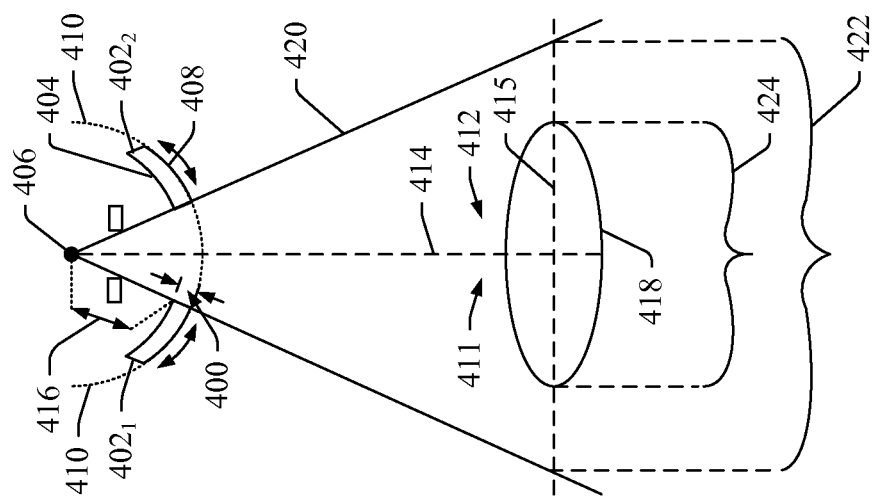

FIG. 4 illustrates an example of the dynamic filter 314. In this example, the filter 314 includes at least a first region $402_1$ and a second region $402_2$, collectively referred to as filter regions 402. The filter regions 402 are disposed on opposing sides 411 and 412 of an imaginary line 414 extending perpendicularly from the focal spot 406 to the a generally planar or flat imaging plane 415. Each of filter regions 402 is a cylindrical volume of substantially uniform (e.g., the same) thickness 400 having a same or constant homogeneity. In the illustrated embodiment, each of the filter regions 402 has a concave side 404 facing the focal spot 406 and an opposing convex side 408 facing the detector array 316.

With respect to the concave side 404, a distance 416 from points along the side 404 to the focal spot 406 is substantially the same along the filter regions 402. The illustrated filter regions 402 are configured to move, independently or in combination, along arc shaped paths 410, with respect to the focal spot 406, towards and away from the imaginary line 414, thereby changing the distance therebetween and hence the attenuation profile. In the illustrated embodiment, where the filter regions 402 have the same thickness 400, the attenuation profile is binary in that radiation is either filtered by the uniform thickness or not filtered by the filter 314. Generally, the filter 314 filters only the outer or peripheral regions of a radiation beam.

Figure 5:
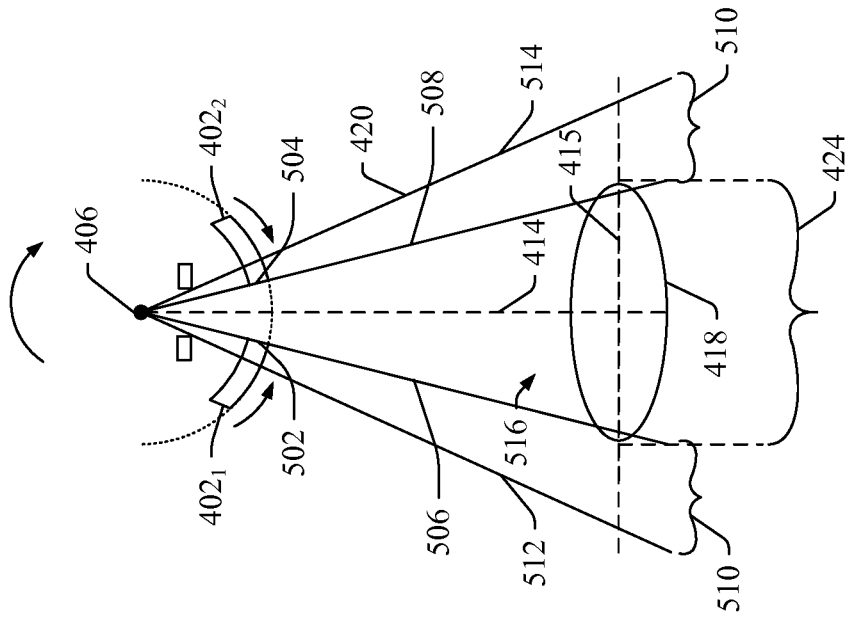
FIGS. 4, 5 and 6 illustrate an example of the dynamic filter in connection with symmetric filter region movement.
Figure 6:
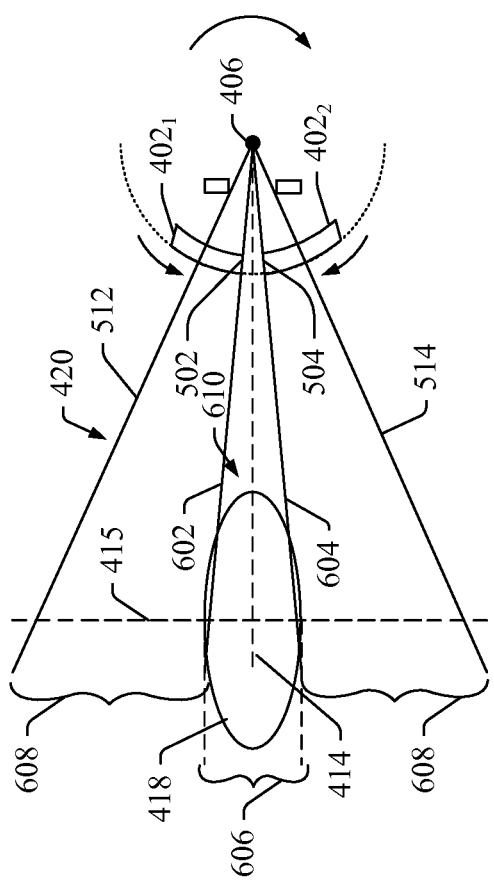

FIGS. 4, 5 and 6 graphically show an example of dynamically adjusting the regions 402 of the filter 314 in accordance with an object 418. In this example, the object 418 is centered in the imaginary line 414. In FIG. 4, the beam 420 is collimated such that a width 422 of the beam 420 at the imaging plane 415 is wider than a width 424 of the object 418, and the regions 402 are positioned such that the filter 314 is not filtering any of the beam 420. This particular configuration is for explanatory purposes, and the regions 402 may be otherwise initially positioned.

In FIG. 5, the focal spot 406 is moving through the twelve o'clock position, and the regions 402 are moved along the paths 410 towards the imaginary line 414. In this example, the regions 402 are moved until edges 502 and 504 respectively substantially align with rays 506 and 508 traversing paths within and near the edges of the perimeter of the object 418 at the width 424 of the object 418. Note that the filtering of the rays traversing the object at the edges does not prevent imaging of these regions. Of course, the edges 502 and 504 may be otherwise aligned, and a margin may be added to ensure the object 418 is adequately scanned, such as margins that would move the regions 402 closer to imaginary line 414, for example, to avoid excessive count rates. In this instance, the filter 314 uniformly filters regions 510 between outer rays 512 and 514 of the beam 420 the rays 506 and 508, and does not filter a region 516 between the rays 506 and 508.

In FIG. 6, the focal spot 406 is moving through the three o'clock position. The regions 402 are moved along the paths 410 towards the imaginary line 414 until the edges 502 and 504 respectively align with rays 602 and 604 traversing paths within and near the edges of the perimeter of the object 418 at a depth 606 of the object 418. In this instance, the filter 314 uniformly filters regions 608 between outer rays 512 and 514 of the beam 420 the rays 602 and 604, and does not filter any portion of a region 610 between rays 602 and 604 within and near the edges of.

With further reference to FIGS. 4-6, the edges 502 and 504 are always parallel to the rays (e.g., 506, 508, 512, 514, 602, and 604) of the beam 420. In addition, it is to be appreciated that the filter regions 402 can be continuously or discretely (at predetermined uniform or non-uniform intervals) dynamically adjusted as the focal spot 406 rotates around the examination region 306 over three hundred and sixty degrees or less.

Various approaches can be utilized to determine where the edges 502 and 504 should be during a given acquisition interval. For example, in one instance one or more 2D and/or 3D pre-scans (e.g., scout, pilot, etc.) are performed and the resulting data is used for planning the scan, including identifying the perimeter of the object 418. In another instance, the perimeter of the object 418 is estimated during scanning based on relative intensity values of the detected data.

Figure 7:
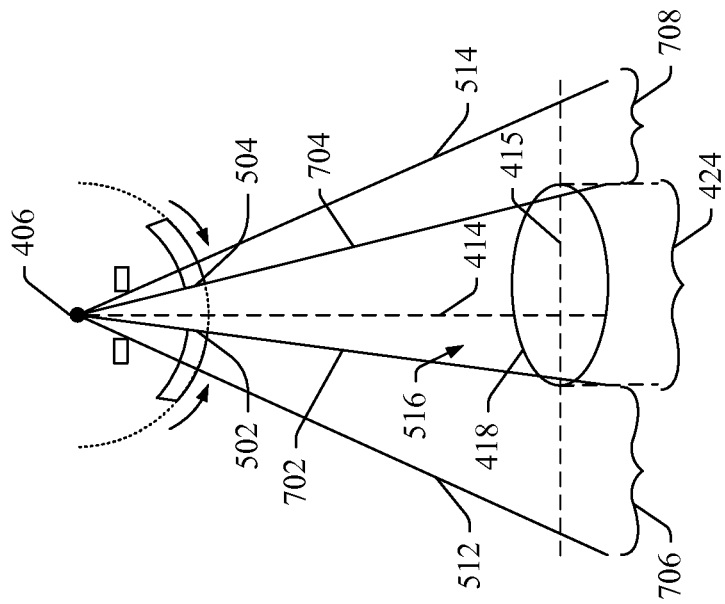
FIG. 7 illustrates an example of the dynamic filter in connection with asymmetric filter region movement.

FIG. 7 graphically shows an example in which the object 418 is positioned off-center with respect to the imaginary center line 414. In this case, the regions 402 are moved through different distances (asymmetrically) and independently in order to align the edges 502 and 504 respectively with rays 702 and 704 traversing paths that cross the perimeter of the object 418 at the width 424 of the object 418. In this instance, the filter 314 uniformly filters regions 706 and 708 between outer rays 512 and 514 of the beam 420 the rays 702 and 704, and does not filter any portion of the region 516.

In FIGS. 3-7, where the thickness 400 and bowtie homogeneity is sufficiently exact and the movement is accurately done, each detector pixel of the detector array 316 may operate under three different conditions: 1) the pixel sees the full flux (no filtering by the filter 314), 2.) the pixel sees reduced flux (filtering by the filter 314), or 3) the pixel is at a position where the flux is partly reduced (partly filtered and partly unfiltered) by the filter 314. Conditions 1 and 2 are stable situations and can be corrected with two different calibration sets. Only a small number of detector pixels will operate in condition 3 within a projection, and, generally, the pixels operating under condition 3 will suffer from unreliable calibration.

During scanning, however, the relative position of the moving regions 402 of the filter 314 can be tracked (e.g., via an encoder or the like) and/or estimated. With this information, the three operating conditions can be identified for each pixel. Depending on the condition, the pixel readings are then either calibrated with a calibration set for condition 1, a calibration set for condition 2, or a hybrid calibration for condition 3. Non-limiting examples of suitable calibrations for condition 3 follow. One or more of the following approaches can be combined or otherwise concurrently employed, and/or one or more of approaches may additionally or alternatively be employed.

In one embodiment, the data calibrator 326 discards the measurements for condition 3 and replaces the measurements with interpolated (e.g., linear or higher order) values based on neighboring pixels falling under condition 1 and/or 2. In another embodiment, the measurements for condition 3 may be calibrated with an estimated calibration set based on the calibration sets for conditions 1 and 2. The estimated set may be a simple average of the calibration sets for conditions 1 and 2 or a weighted average in which a higher weight is applied to the calibration set corresponding to the pixel closer to the pixel under condition 3. In other words, the calibration may be blended from calibration set 1 to calibration set 2 by moving from the calibration set for condition 1 and the calibration set for condition 2. In another embodiment, the reconstructor 318 employs an iterative algorithm in which pixels under condition 3 are rejected or weighted down to limit their impact.

With scan protocols in which projections are acquired over three hundred and sixty degrees, each ray is measured twice, but in opposite directions. With such protocols, the filter regions 402 can be moved so that at least one of the two redundant measurements falls under condition 1 or condition 2. Where the other of the two redundant measurements falls under condition 3, that measurement can be discarded and replaced with the redundant measurement falling under condition 1 or condition 2.

Figure 8:
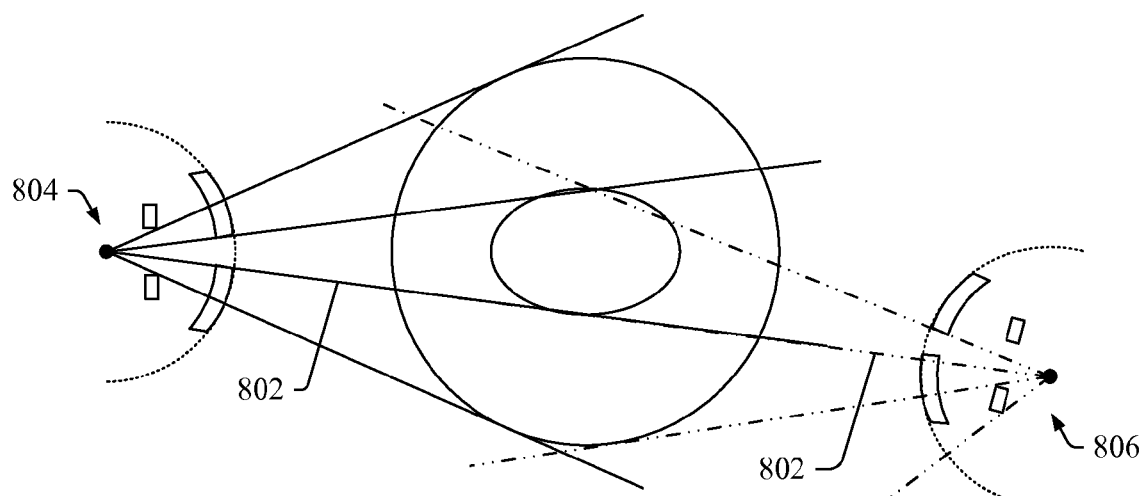
FIG. 8 illustrates an example of differently filtering a ray detected in opposing direction using the dynamic filter.

This is shown in FIG. 8 where ray 802 is measured when the focal spot 406 is located at a first position 804 and the ray 802 is also measured when the focal spot 406 is located at a second position 806, after the focal spot has traveled to the opposite side of the scanned object 418. As shown, when measured with the focal spot 406 at the first position 804, the ray 802 falls under condition 3 (the ray 802 traverses along the edge of the filter), and when measured with the focal spot 406 at the second position 806, the ray 802 fall under condition 2 (the ray 802 traverses through and is filtered by the filter).

Figure 9:
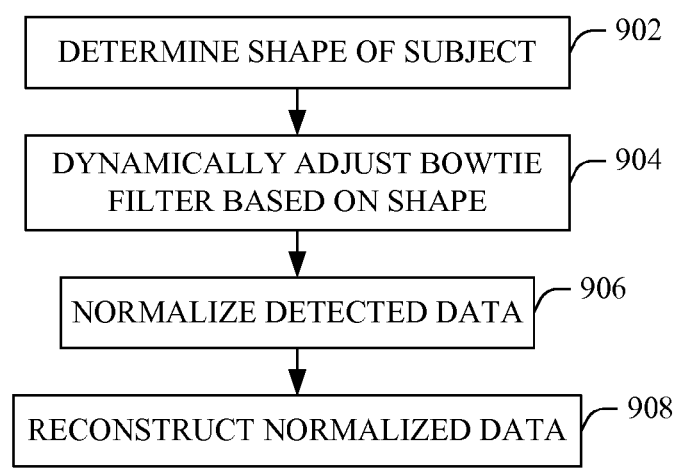
FIG. 9 illustrates an example method.

FIG. 9 illustrates a method. It is to be appreciated that the ordering of the acts is not limiting. As such, in other embodiments, the ordering of the acts may be different. In addition, one or more of the acts can be omitted and/or one or more other acts can be added.

At 902, a shape of a subject (or object) being scanned is determined. As described herein, the shape can be determined via a pre-scan and/or during scanning.

At 904, a dynamic filter is dynamically adjusted during scanning the object or subject based on the determined shape. As described herein, the filter has a constant thickness and a constant homogeneity, and is moved along an arc shaped path relative to the focal spot of the radiation source to change the region of the radiation beam to filter.

At 906, detected data is normalized based on whether a corresponding detector pixel received radiation fully filtered by the filter, radiation not filtered by the filter, or radiation partially filter and partially unfiltered by the filter. As described herein, various approaches can be utilized to normalize the data corresponding to the partially filter and partially unfiltered radiation.

At 908, the normalized data is reconstructed to generate volumetric image data. The volumetric image data can be further processed to generate on or more images.

Figure 1:
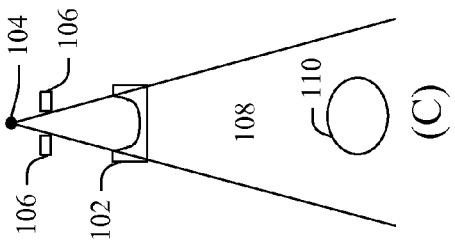
FIG. 1 illustrates a prior art static filter.
Figure 1:
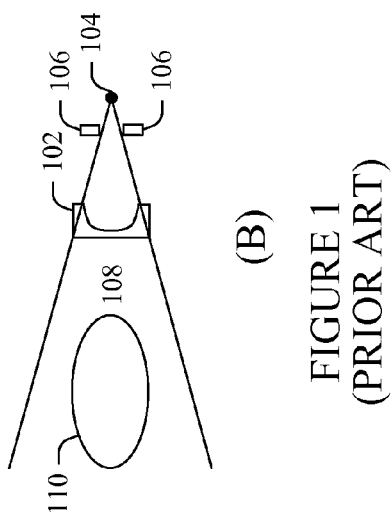
Figure 1:
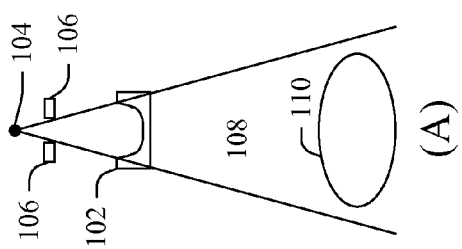
Figure 2:
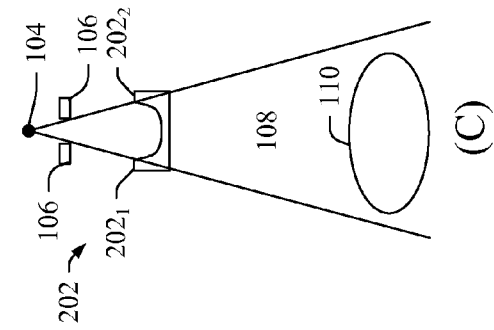
FIG. 2 illustrates a prior art dynamic filter.
Figure 2:
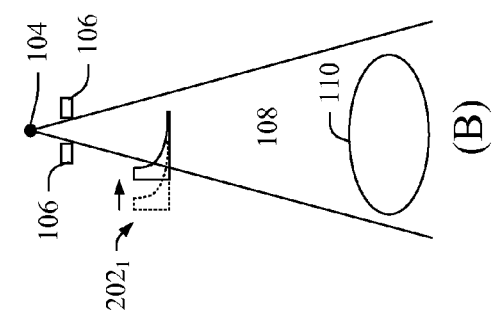
Figure 2:
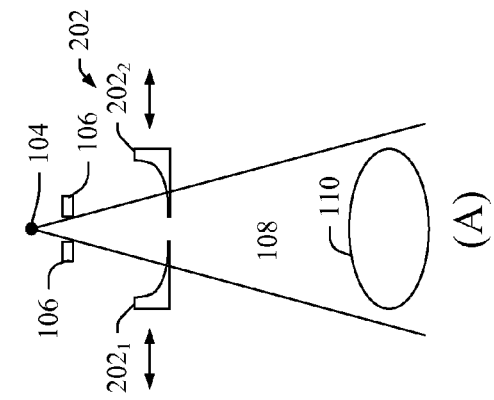

The dynamic filter 314 described herein can be used as, in connection with, and/or in place of a conventional bowtie filter, such as the bowtie filters discussed in conjunction with FIGS. 1 and 2, as well as other bowtie filters.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

What is claimed is:

1. An imaging system, comprising:
a source having a focal spot that emits an x-ray radiation beam collimated by collimator that traverses an examination region;
a radiation sensitive detector array having a plurality of pixels that detects radiation traversing the examination region and generates projection data indicative of the detected radiation;
a filter, disposed between the source with the collimator and the examination region, that filters peripheral regions of the emitted x-ray radiation, wherein the filter includes two separate and moveable regions, each region having a substantially same thickness and constant homogeneity,
wherein each of the filter regions is configured to move along an arc shaped path about the focal spot, which changes an attenuation profile of the filter; wherein each of the filter regions is configured to dynamically move in accordance with a shape of an object or subject during scanning of the object or subject, and wherein the shape of the object or subject is determined based on one or more pre-scans of the object or subject; and
a reconstructor that calibrates a detector pixel receiving partially filtered radiation using a hybrid calibration algorithm by detecting a same ray of the x-ray radiation beam from two opposing different directions, wherein a measurement from one of the directions includes partially filtered and partially unfiltered radiation, and a measurement from the other direction includes either fully filtered or fully unfiltered radiation; and replacing the measurement corresponding to the partially filtered and partially unfiltered radiation with the measurement corresponding to the fully filtered or fully unfiltered radiation.

2. The system of claim 1, wherein each of the filter regions is cylindrically shaped and has an edge that is always substantially parallel to a ray of the emitted radiation beam when the filter regions are filtering the x-ray radiation beam.

3. The system of claim 1, wherein each of the filter regions has substantially a same radiation attenuation characteristic.

4. The system of claim 1, wherein the filter regions are concurrently moved in coordination.

5. The system of claim 1, wherein the filter regions are asymmetrically moved.

6. The system of claim 1, wherein the shape of the object or subject is determined during scanning based on generated data.

7. A method, comprising:
   filtering peripheral rays, of an emitted x-ray radiation beam collimated by a collimator traversing an examination region, which substantially do not traverse an object or subject in the examination region, with a dynamically adjustable filter having a substantially same thickness and homogeneity along the filter; and
   calibrating a detector pixel receiving partially filtered radiation using a hybrid calibration algorithm by:
      detecting a same ray of the x-ray radiation beam from two opposing different directions, wherein a measurement from one of the directions includes partially filtered and partially unfiltered radiation, and a measurement from the other direction includes either fully filtered or fully unfiltered radiation; and
      replacing the measurement corresponding to the partially filtered and partially unfiltered radiation with the measurement corresponding to the fully filtered or fully unfiltered radiation.

8. The method of claim 7, wherein an edge of the filter is substantially parallel to a ray of the emitted x-ray radiation.

9. The method of claim 7, further comprising:
   moving filter regions along respective arc shaped paths about a focal spot, thereby changing an attenuation profile of the filter in coordination with a shape of an object or subject being scanned.

10. The method of claim 7, wherein the calibration algorithm includes replacing a measurement of a pixel with a value determined by an interpolating measurement based on neighboring pixels that receive either fully filtered or unfiltered radiation.

11. The method of claim 7, wherein the calibration algorithm is estimated based on a calibration for pixels receiving fully filtered radiation and a calibration for pixels receiving unfiltered radiation.

12. The method of claim 11, wherein the estimated calibration algorithm includes a weighted combination of the calibration for pixels receiving fully filtered radiation and the calibration for pixels receiving unfiltered radiation.

13. The method of claim 7, wherein the calibration algorithm includes discarding or weighting down a pixel while performing an iterative reconstruction.

\* \* \* \* \*